United States Patent [19]

Stone et al.

[11] 3,934,226
[45] Jan. 20, 1976

[54] AUTOMATED AUDIO HEALTH HISTORY ACQUISITION SYSTEM

[75] Inventors: Stanford C. Stone, Deerfield; Irwin H. Sommerfeld, Mount Prospect, both of Ill.

[73] Assignee: International Health Systems, Inc., Rolling Meadows, Ill.

[22] Filed: Nov. 23, 1973

[21] Appl. No.: 418,660

Related U.S. Application Data

[63] Continuation-in-part of Ser. No. 199,711, Nov. 17, 1971, abandoned.

[52] U.S. Cl. ............................. 340/172.5; 35/9 A
[51] Int. Cl.² ....................... G06F 3/16; G09B 7/06
[58] Field of Search ................... 35/9 A; 340/172.5

[56] References Cited
UNITED STATES PATENTS

| | | | |
|---|---|---|---|
| 3,273,260 | 9/1966 | Walker | 35/9 A |
| 3,277,588 | 10/1966 | Lynott et al. | 35/9 A |
| 3,369,307 | 2/1968 | Shupp | 35/9 A |
| 3,407,513 | 10/1968 | Conn | 35/9 A |
| 3,708,891 | 1/1973 | Rosov | 35/9 A |
| 3,737,863 | 6/1973 | Rowland et al. | 340/172.5 |
| R27,580 | 2/1973 | Rawson et al. | 340/172.5 |

*Primary Examiner*—Joseph M. Thesz, Jr.
*Attorney, Agent, or Firm*—Silverman & Cass, Ltd.

[57] ABSTRACT

The system includes a multi-track tape player with a set of head phones which are connected to the audio output of the player and are located in a history-taking booth for use by a patient. A two-track tape is mounted in the tape player and includes a first track having a plurality of questions recorded thereon in a predetermined sequence and a second track having a plurality of code signals recorded thereon, each code signal identifying a particular question recorded on the first track. A patient viewing and response device is located in the booth and includes a keyboard response panel and scale models of the human body adapted to depict typical pain or discomfort patterns. The patient response device is selectively operable by a patient for giving one of several predetermined answers to each question audibly presented to the patient. The device and the player are connected to a computer which controls the audio presentation of the successive questions relative to the answers given to previous questions. A printer is connected to the computer for providing a printed read-out of the questions and answers. The system is activated by the patient or an operator.

12 Claims, 6 Drawing Figures

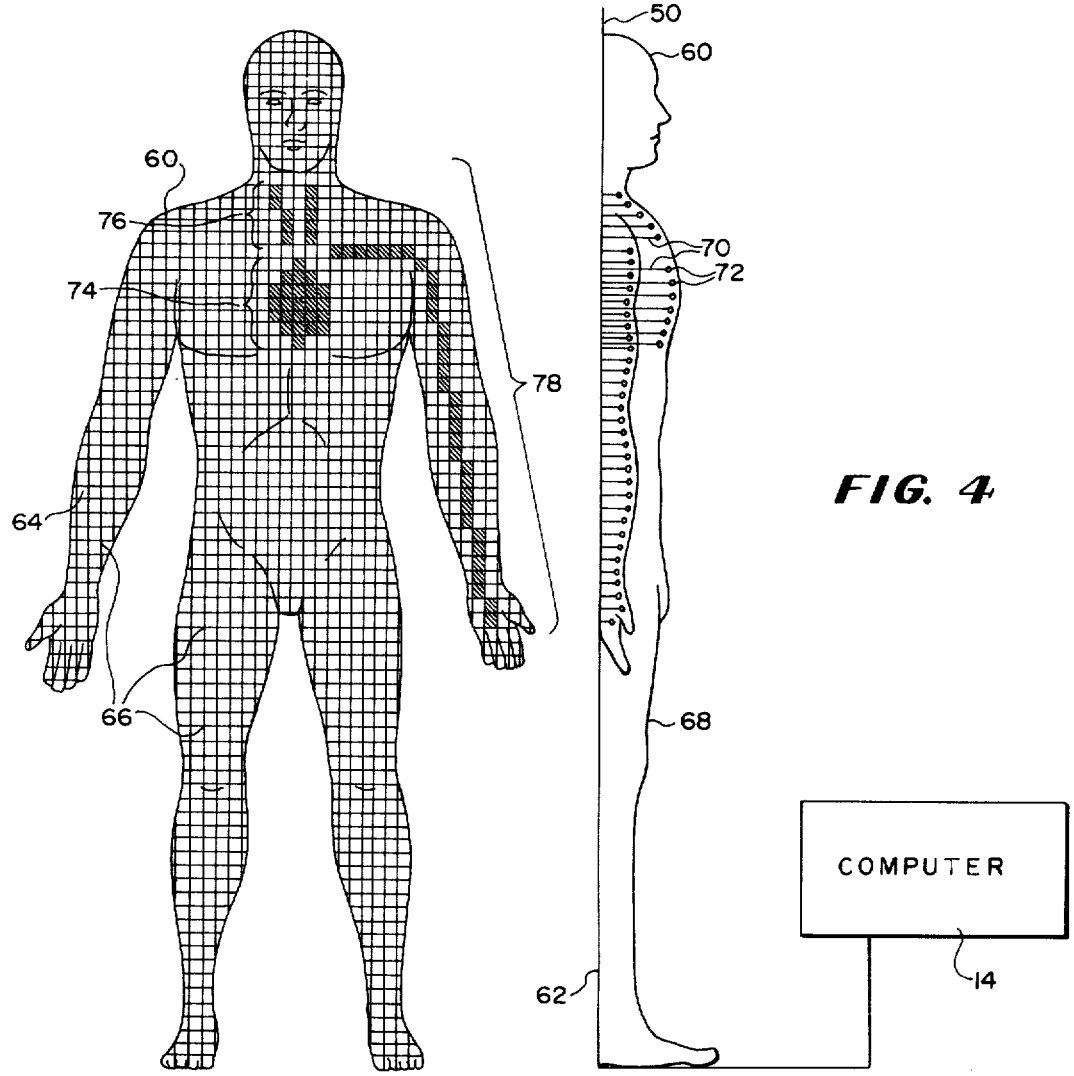
FIG. 3
FIG. 4
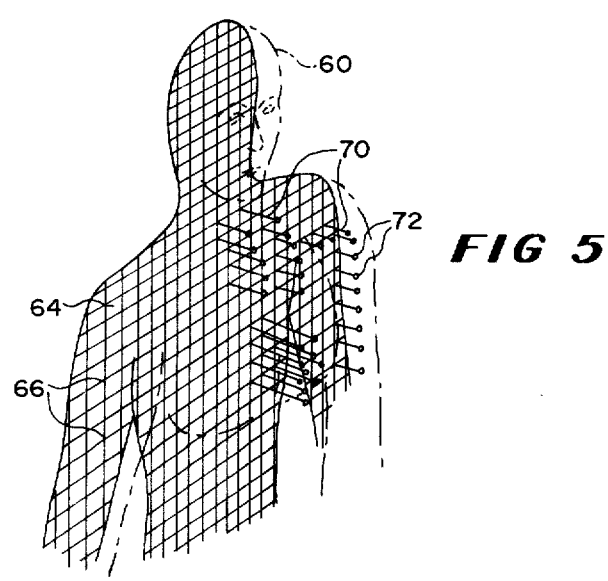
FIG 5

AUTOMATED AUDIO HEALTH HISTORY ACQUISITION SYSTEM

CROSS REFERENCE TO RELATED APPLICATION

This application is a continuation-in-part of our co-pending U.S. application Ser. No. 199,711, filed Nov. 17, 1971, now abandoned and assigned to the same assignee of the present application.

BACKGROUND OF THE INVENTION

The present invention relates to automated medical history taking systems and particularly to an audio health history acquisition system wherein questions are presented audibly to a patient.

Heretofore it has been proposed that a medical or health history be taken from patients automatically by devices which include means for automatically processing the answers given by a patient in response to questions presented to him. Such systems would typically include a computer and be in the nature of a data processing system. Typically such history taking devices are utilized in multiphasic health testing systems. One such device presently in use provides for a visual display of the question being asked on a cathode-ray tube with the patient answering the question by depressing one of four buttons adjacent four written answers. These answers are YES, NO, I DON'T KNOW, or REPEAT.

In some instances questions are displayed on a screen through the medium of a carrousel slide projector containing a plurality of slides each slide having a specific question or questions thereon. In other instances, the visual display on a cathode-ray tube is generated directly from and by a computer.

Most of the presently known history-taking devices have a "chain branching capacity" which is activated by the answer given by the patient to a specific question. In this respect if a patient answers a question "YES", he may then be required to answer a plurality of other questions which are not in the direct chain of questions but rather in a branch chain of questions. One illustration of such a device is disclosed in U.S. Pat. No. 3,708,891 which utilizes teletype modulation signals on a pre-recorded magnetic tape representing statements corresponding to alternative responses of an individual to questions. In the device of U.S. Pat. No. 3,708,891, the response of the individual is typed together with the question immediately after the response is given. In addition, most history-taking devices also have the capability of skipping questions that may not be applicable to a particular patient, such as, for example, sex-oriented questions which relate solely to the male sex or the female sex. Thus, once the patient answers "YES" or "NO" to the question "Are you male?", or the question "Are you female?", the history taking device, in response to the answer given, will skip certain questions. Many history-taking devices also include the capability of repeating the visual display of the question. Two examples of medical history-taking systems or devices of the type just described can be found in U.S. Pat. Nos. 3,566,365 and 3,566,370.

In many instances, the presently known automated history taking devices have not been effective in obtaining the desired information from a patient. In this respect, it has become apparent that a major drawback or shortcoming encountered with presently available automated history taking devices resides in the fact that many patients are unable to read and/or unable to comprehend the question which is presented to them in a visual manner. Thus, it is the principal object of the present invention to provide another means, specifically an audio means, for audibly presenting questions to a patient.

Although the audio presentation of a question to a subject is known in the field of teaching machines — see, for example, U.S. Pat. No. 3,484,950 — such audio presentation of questions has not been utilized in or suggested for use in automated medical history taking systems. By audibly presenting questions to a patient, the problem of poor reading ability and/or comprehension is overcome. This problem is oftentimes very acute since many people cannot understand the written language. The provision of an audible presentation of questions also permits the utilization of local dialects involved in a particular locale or of different languages whereby the questions used are presented in a dialect or language which can be easily understood and answered by the patient. The need for such a means for audibly presenting questions in an automated medical history acquisition system can be readily appreciated by the fact that those persons who are in most need of medical help are those who are poor, uneducated or members of minority groups who converse in a local dialect or ethnic language.

Another object of the present invention is to permit in an automated medical history acquisition system, the development of a comprehesive questionnaire library on casette type tapes with actual segmentation into various areas.

Another object of the present invention is to provide an automated audio health history acquisition system which is adapted to provide a complete health history printed read-out of the questions presented to a particular patient and the answers provided by the patient. The printed read-out will also identify the patient who gave the answers. The printed read-out normally will be effected after the total series of questions and answers has been presented to and received from the patient so that a complete history of the patient's health will be reproduced on one printed record.

A further object of the invention is to provide a system including one or more reduced-scale models of the human body which are viewable by the patient while he is listening to the questions. Certain typical pain or discomfort patterns will be displayed on the models for identification by the patient as to whether he has experienced the same.

Still another object of the present invention is to provide an audio health history acquisition system which will permit the generation of a particular history by the user of a system to suit his own requirements. For example, the system may be used in the admitting room of an emergency ward of a hospital for obtaining a short quick medical history from an incoming patient. On the other hand, the system can be used in a doctor's office for obtaining a much longer medical history from patients of the doctor. In this use of the system of the invention, the questions can be recroded on a magnetic tape in the doctor's voice so that the questions will be presented to a patient in a familiar voice. By hearing the questions in a familiar voice, the patient will be at ease and more inclined to answer the questions fully and correctly.

A still further object of the invention is to provide a telephone dial overlay member transforming the telephone dial to a patient response keyboard to enable the taking of a patient's health history from any remote area in which telephone facilities are available.

Other objects and advantages of the invention will appear to those skilled in the art from the ensuing disclosure and drawings.

SUMMARY OF THE INVENTION

According to the invention, there is provided an automated audio health history acquisition system including a mechanism for storing questions in a predetermined sequence, a mechanism for storing a code signal identifying each question, a mechanism for audibly presenting each question in the predetermined sequence and for simultaneously transmitting the code signals, and a mechanism permitting the patient to selectively answer each question by one of a series of predetermined answers. A control mechanism is connected to the mechanism for audibly presenting the questions and to the mechanism for answering the questions, and is adapted to control the presentation of each question relative to the answer received by the control mechanism for the previous question. The control means includes a storage device for receiving and storing the transmitted code signals identifying each question, and the answer to each question. Preferably the system includes a read-out device for providing a read-out of the questions and answers. The read-out will also identify the patient who gave the answers. Also, preferably, the system includes a device for activating the control mechanism and for identifying the patient to the control mechanism.

The invention also provides scaled size models of the human body viewable by the patient and adapted to display typical pain or discomfort patterns on the surface of the models for identification by the patient as to whether he has experienced the displayed pain or discomfort patterns. The control mechanism directs which patterns will be displayed to the patient.

There also is provided a telephone dial overlay member for use with a standard telephone set to convert the dial thereof to a patient response keyboard. The overlay member is such that a health history may be taken from a patient at a location remote from the control mechanism of the system.

BRIEF DESCRIPTION OF THE DRAWINGS

FIG. 3 is an enlarged front view of one of the models of FIG. 2 illustrating a typical pain or discomfort pattern illuminated thereon;

FIG. 4 is a side view of the model of FIG. 3 illustrating connection thereof to the computer of the invention;

FIG. 5 is a fragmentary perspective view of the model of FIGS. 3 and 4; and

DESCRIPTION OF THE PREFERRED EMBODIMENT

Figure 1:
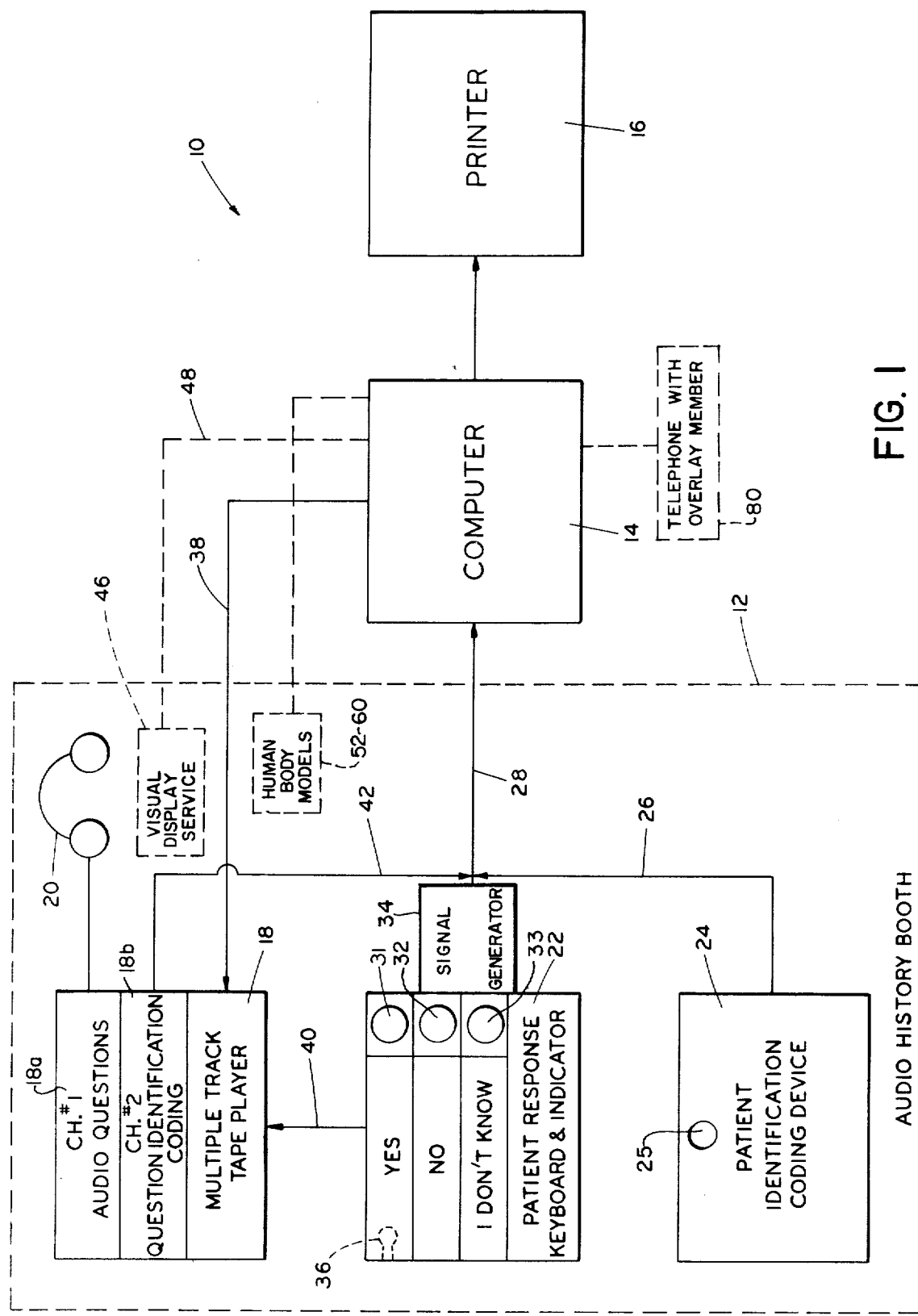
FIG. 1 is a schematic block diagram of the automated audio health history acquisition system of the invention.
Figure 2:
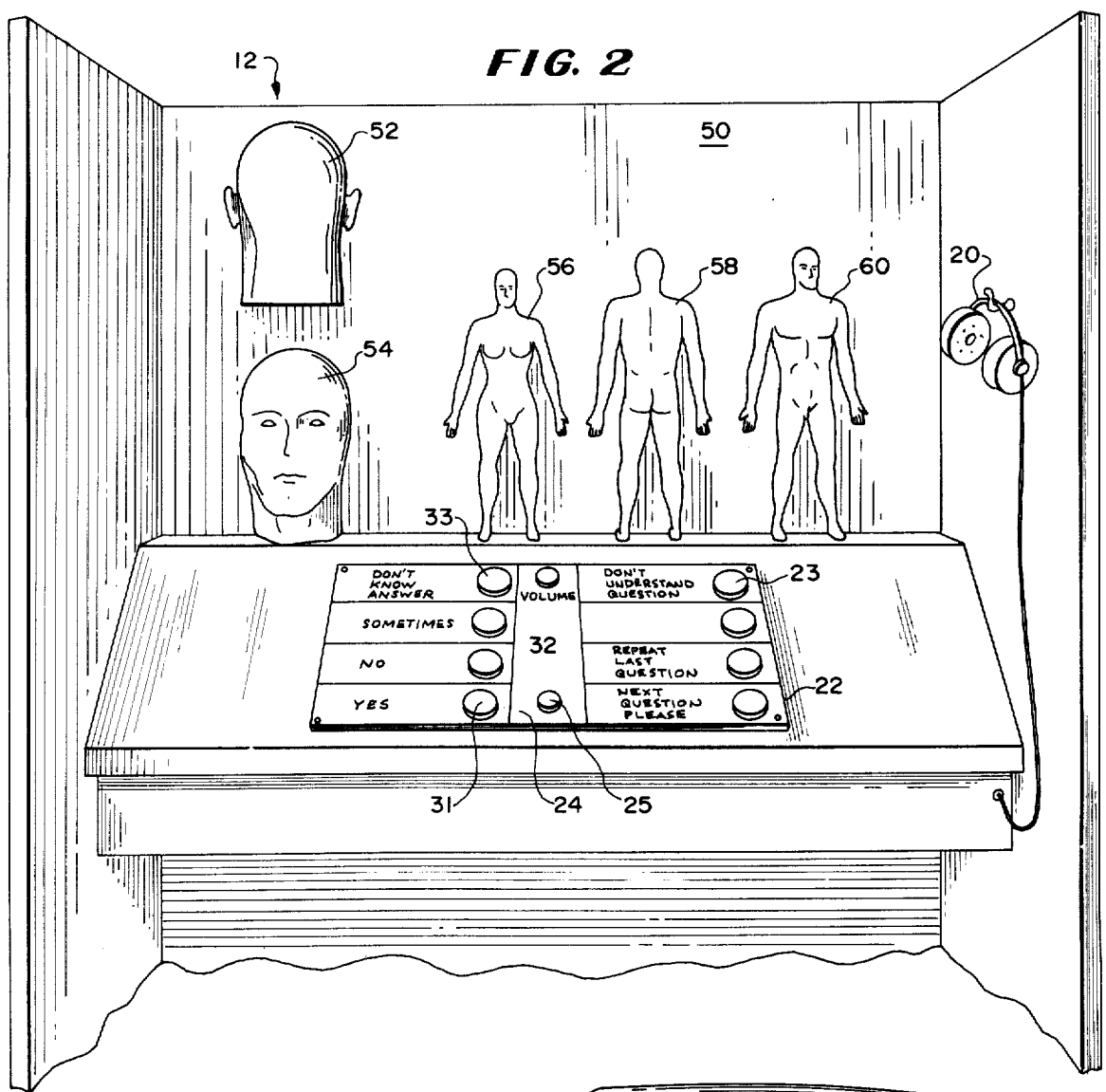
FIG. 2 is a fragmentary perspective view of a booth having the keyboard and scaled size human figure models of the invention.

In FIG. 1, the system of the invention is generally indicated at 10 and includes an audio history booth schematically shown with broken lines at 12. The booth 12 also is illustrated in FIG. 2. As will be explained in detail hereinafter, the audio history booth 12 is connected to a computer 14 which in turn is connected to a printer 16. Depending upon the capability of the computer, one or more audio history booths 12 can be connected to the computer 14, although in the illustrated embodiment only one such booth 12 is shown connected to the computer 14.

In the booth is a multi-track tape player 18 which has a pair of earphones 20 connected to the audio output thereof. Although not shown, it will be understood that the multi-track tape player 18 is adapted to store therein a reel of magnetic tape having two channels or tracks thereon shown schematically at 18a and 18b. One channel — the first channel 18a — will have audio questions recorded thereon and the second channel 18b will have question identification code signals recorded thereon. In this respect when a question is recorded on the first channel 18a of the tape, an identifying code signal is simultaneously recorded on the second channel 18b of the tape.

The booth 12 also includes a patient response device 22 having a keyboard and indicator, and a patient identification and coding device 24.

The device 24 can take one of several forms. For example, it can be of the type which receives and senses an identifying object or card carried by the patient. Preferably, however, the device 24 includes a thumb wheel operated programmable digit switch for establishing a binary coded patient identification number, and a switch or button 25 for operating a suitable mechanism for transmitting a signal containing the binary coded number via a line 26 to an input line 28 to the computer 14. The digit switch is set by the patient or an operator.

The code information thus sent to the computer 14 will perform two functions. First of all, it will activate the computer to operate the tape player 18 to audibly present questions to the patient via the headphones 20 which the patient has placed on his head. Secondly, the code signal will identify to the computer the patient who is answering the questions. This code signal identifying the patient is stored in the computer and will be transmitted to the printer 16 when the computer is operated to provide a printed read-out of the questions and answers.

After a patient hears a question, he will press one of three buttons 31–33 on the keyboard of the patient response device 22. Each button 31–33 is disposed adjacent a printed answer, YES, NO or I DON'T KNOW and is connected to a signal generating mechanism shown schematically at 34 for generating a signal identifying the answer given which signal is sent to the computer 14 via line 28. Preferably, and as indicated by phantom lines at 36, an annunciator light is disposed under a translucent panel having the predetermined answer YES, NO or I DON'T KNOW written thereon so that when and as a patient depresses a particular answer button 31, 32 or 33, the specific answer he has given will be illuminated. Other answers are available to the patient as illustrated in FIG. 2 on the keyboard 22.

It will be understood that the computer 14 controls the operation of the player 18 by means of control signals which are generated in the computer and sent via a control line 38 to the player 18. The control signal will activate the player 18 to present one question at a time to the patient. In this respect the patient will not hear a succeeding question until he has given an answer to the question presented to him. If the patient doesn't answer the question, the computer could be programmed to send another signal to repeat that question. Alternatively, a repeat button can be provided on the keyboard 22 to permit the patient to cause the tape player to repeat the question. Such a repeat button 23 is shown in FIG. 2. A control line from the device 22 to the player 18 for this purpose is indicated at 40.

At the same time that a specific question is being presented to a patient, a code signal identifying that question is sensed on the second track of the tape and sent from the player 18 via an input line 42 and the input line 28 to the computer 14. This question identifying code signal is then stored in the computer and is correlated with the answer given by the patient which is transmitted from the device 22 via the input line 28 to the computer. It would be understood that for this purpose the computer includes a plurality of register circuits for storing the code signals identifying each question and the corresponding answer to each question by the patient as well as the code information identifying the patient.

In addition to the health history questions which orally are presented to the patient in the booth 12, the invention contemplates use of human figure models for display to the patient of typical pain or discomfort patterns. The patient sitting in booth 12 (FIG. 2) faces wall 50 on which are positioned several human body three-dimensional models or figures of reduced-scale size. There are rear and front head models 52, 54, a front female body model 56, a front male body model 58 and a rear body model 60. Each of the models 52–60 is formed from a three-dimensional figure which has been sliced transversely to provide a flat surface which is mounted on wall 50. The models 52–60 are constructed of plastic or other suitable material and may be of clear or, preferably, opaque surface coloring.

Looking at FIGS. 3–5, one of the full-body models 60 is shown for purposes of illustrating the manner in which pain patterns are displayed to the patient. The description which follows applies equally to the other models 52–58. The model 60 is provided on the wall-facing surface 62 thereof with a grid pattern or matrix 64 or electrical circuitry having junction points 66 spread throughout the model profile. Where the outer surface 68 of the model 60 is opaque the grid patterns 64 would not be visible to the patient facing same. Originating from predetermined selected junction points 66 are a series of energy transmission conduits or lines 70 which extend to the inside of surface 68 and terminate at light emitting elements 72. In the embodiment shown, transmission lines 70 are electrical wires and light emitting elements 72 are bulbs. Alternatively, the lines 70 could be fiber-optic bundles terminating at points 72 to emit light from bulbs or LEDs positioned at the junction points 66; other types of light-transmission devices could be used to achieve the purpose of display of light patterns on the surface of model 60. It is to be noted that the light sources 72 extend to and are positioned near the surface 68 of the model to avoid parallax error which might result as the patient viewed the model while shifting his location; such parallax error would result if the light sources were positioned directly on matrix 64 spaced from surface 68.

The display of light patterns on the surface of model 60 is operable by the computer 14 which is programmed to cause selected bulbs 72 to illuminate in accordance with pre-determined questions presented to a patient and his response. As an illustration, a first question would be: "Are you a male?" Depression if "yes" button 31 by the patient would signal computer 14 to feed light excitation energy to model 60 of the male figure on selected ensuing questions. One such ensuing question would then be: "Have you experienced pain in the chest as shown on the model.?" While the question is being presented through earphones 20, the computer would cause bulbs 72 to be illuminated in the area 74 to indicate the chest area at which the question is directed. A "yes" response to this question would direct the computer, through its program, to cause the next question, "Has the pain extended into your neck?" to be presented; simultaneously the computer would maintain illumination of area 74 and cause bulbs 72 in the area 76 to beome illuninated. If the patient responds "yes" to this question, the bulbs along area 78 would be programmed to light up and the question "Has the pain extended into the left arm as shown?" would be asked.

It will be understood from the above description that a wide variety of questions may be asked with corresponding light activation illustrations to the patient. The models 52–60 serve visually to depict pain or discomfort patterns so as to elicit a response from the patient through the keyboard response panel 22. The illumination areas may be discrete with high resolution or may be grossly lighted; they may be dynamic so as to simulate shooting pains or static as desired. The computer 14 is capable of causing any of many light patterns to be depicted and changes may be made by designing appropriate computer software using the structure described. Because of the computer control, "body branching" illumination is possible as described with the three questions mentioned above; if any question is answered "no", the computer would cause all lights to go out so that a next series of questions could be presented.

After a patient has finished answering all the questions, the computer will terminate operation of the tape player and will, in some way, indicate to the patient that the questioning is over. For example, the computer can cause lighting in the booth to dim or go off completely. Alternatively, the first channel of the tape can have a message recorded at the end of a series of questions advising the patient that the questioning is finished.

Depending upon the capability of the computer, the printed read-out of the questions and of the answers to those questions by a particular patient can be obtained immediately or at a later period of time. If it is not obtained immediately, the computer, of course, must have means for storing additional sets of answers to these questions obtained from subsequent patients who are interviewed in the audio history booth 12.

Although the tape player 18 has been shown as being mounted in the booth 12, it is to be understood that it can be mounted outside of the booth. Also, it is to be understood that advancement of the tape player to present a succeeding question on the first channel of the tape, can be controlled by the patient within the booth if desired. In this respect, control information for operating the player can be advanced from the device 22 via the line 40 by depression of a button (not shown) on the device 22. Also, if desired, the patient response keyboard and indicator divice can include other means beside annunciator lights 36 for indicating to the patient the answer he has given. For example, a short record such as the type utilized in talking toys can be utilized for providing an audible indication to the patient of the answer he has given. In this respect, each button 31, 32, 33 or the others shown on the keyboard of the device 22 can be connected to a mechanism for operating a transducer such that when the patient depresses one of the buttons, he will not only generate a signal indicating the answer he has given, which is transmitted via the input line 28 to the computer 14, but will also activate the transducer mechanism which will audibly feedback to the patient the answer he has given.

It will be apparent from the foregoing description that a patient taking the audio history and responding to the questions requires only two elements (except for the models 52–60) at his location, these being the sound transmission member or headphones 20 and the response keyboard 22 with suitable buttons, levers or the like to indicate a response to a question. These two elements may be located remote from the other elements of the system to enable taking of a health history from a patient who is not able to travel to the situs of the booth 12. For this purpose a standard telephone handset may be adapted for taking health histories from remote locations.

Figure 6:
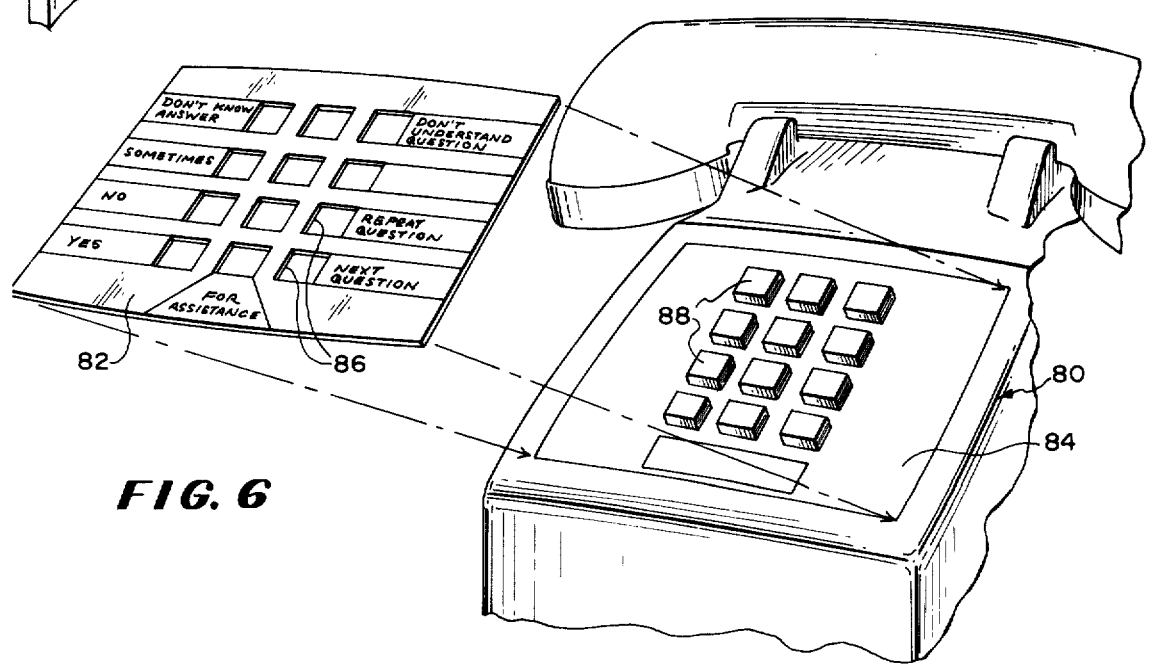
FIG. 6 is an exploded perspective view of a telephone casing with the dial overlay member of the invention shown for positioning thereon.

In FIG. 6 such a standard Touch Tone telephone handset 80 is shown. A dial-face overlay member 82 is provided for positioning on the dial-face 84 of the telephone. Overlay member 82 has openings 86 corresponding in number and orientation to permit buttons 88 to pass therethrough and extend thereabove. The overlay 82 includes legends or indicia for designating particular responses which may be given by a patient to a question asked. The legends on the overlay 82 correspond to those of the keyboard 22 in booth 12. In order to give his health history, the patient would call the location of the health history booth 12 and an operator at that location would position the called telephone reciever in a sound data conversion device connected to computer 14. Such sound data conversion devices are well-known. The operator would then activate the computer to start tape player 18 which would present questions to the patient over his telephone receiver. Responses to the questions would be effected by depressing appropriate buttons 88 according to the legends on overlay 82. The tone emitted by the patient's telephone would be received by the computer and cause the same to operate in the same manner as depressing a button on keyboard 22 would do. All other operational aspects of the system of the invention would remain unchanged.

In instances where a dial-type telephone only is available to the patient, he could be provided with an auxiliary Touch Tone key pad and tone assembly (not shown) which may be coupled to the telephone mouthpiece to accomplish the response communication to the health history booth 12.

Although a preferred embodiment of the system of the invention has been described in the foregoing description with reference to the attached drawings, it is to be understood that obvious modifications and variations can be made to the system 10 of the invention without departing from the spirit or scope of the invention. For example, a visual display device can be mounted in the audio history booth as indicated by phantom lines at 46. The visual display device 46 can then be adapted to be operated by the computer 14 for presenting a visual display of a question simultaneously with the audible presentation of the question by the player 18. Such simultaneous audible and visual presentation of questions to a patient will further enhance the ability of the patient to understand and comprehend the question and thereby better enable the patient to properly answer the question.

It will be noted that by using a computer such as a minicomputer which can, if desired, be stored in the booth for controlling the operation of the multi-track player, any changes in the format of the questions presented will only require a change in the program of the computer and the question on the tape. In other words, the only change would be in the generation of software in terms of questions to be asked, the order of the questions, and the storage of the order (a question) in the computer. The basic hardware involved in the system would not need to be changed.

Also, it is to be understood that the tape player can be a tape player and recorder which can be of a closed loop type or of the reversible casette type. The electronic circuitry of the tape player is such that the tape can be played in the forward or reverse mode. In this respect, the movement of the tape to go forward to the next question or to go in the reverse direction for the repeating of a question can be controlled by the computer or by the patient.

By utilizing a tape player and a tape for storing the questions, the number of questions can be adjusted as desired. In this respect, for certain applications, it is desirable to have short medical histories taken whereas in other applications it is desirable that a comprehensive medical history be taken. Also, the span of time over which the questions are asked can be adjusted to the average attention span of the patients being interviewed.

Additionally, although the invention has been described as utilizing two tracks on a tape, it is to be understood that the questions and identifying code signals can be both recorded on one track of the tape.

The various elements of the system 10 are disclosed with reference to their generic names and are available commercially from numerous sources. For purposes of illustration only, the following comprises a list of such elements and the source thereof which has been determined to be acceptable for incorporation into the system of the invention:

Computer 14 may be a "digital PDP-8/e" computer sold by Digital Equipment Corporation, Maynard, Massachusetts.

Printer 16 may be a Model 33ASR on 33 KSR teletype device sold by RCA Service Company, Camden, New Jersey.

Tape player 18 may be a "digital cassette tape device" Model No. DGM 10-31 sold by Braemar Computer Devices, Inc., Minneapolis, Minnesota.

Coding device 24 may be a Model L 10-02A2 lever-wheel switch (U.S. Pat. No. 3,499,127) sold by Cherry Electrical Products, Waukegan, Illinois.

Button switchs 31–33 may be type 518 base and type 411 cap switches sold by MARCO-OAK, Anaheim, California.

Electrical circuits in signal generating mechanism 34 may be Master-Slave Binaries SP 322B circuits and Data Selector Ser. No. 74150 N sold by Signetics, Sunnyvale, California.

From the foregoing description it will be apparent that the automated audio health history acquisition system of the invention has a number of advantages some of which have been set forth above, and others of which are inherent in the invention. Accordingly, the scope of the invention is only to be limited as necessitated by the accompanying claims.

What is desired to be secured by Letters Patent of the United States is:

1. An automated audio health history acquisition system for audibly presenting health history questions to a patient and recording responsive answers thereto, said system comprising:
   A. a computer having a plurality of register circuits for storing code signals and transmitting code signal operation instructions,
   B. a patient identification coding device for initally establishing and generating a patient identification code signal and transmitting the same to the computer for storage therein, the patient identification coding device including an actuating device for activating the computer,
   C. a multi-channel recorder with audio output operable by signals generated by said computer after the patient identification code signal has been initiated, said recorder including
      i. a first memory channel having said questions recorded thereon in a predetermined sequence to be audibly presented one question at a time to the patient,
      ii. a simultaneously operable second memory channel having code signals recorded thereon to identify each question recorded on said first channel and transmit to the computer said question code signals,
   D. at least one human figure model for visual display to the patient, the model having a front three-dimensional surface and a rear planar surface, the rear surface being formed with a matrix of electrical circuitry having junction points spread throughout the surface thereof, a plurality of energy transmitting conduits originating from selected ones of the junction points and terminating with light emitting elements at selected points proximate the front surface of the model, the matrix being controllably connected with the computer,
   E. a patient response device for receiving the audio output of the first channel and including
      i. a keyboard operable by the patient in response to the questions to selectively indicate answers to said questions by one of a series of predetermined answers,
      ii. an answer code signal generator for generating code signals according to the patient indicated answer and transmitting the same to the computer for correlated storage with the respective question code signals, and
   F. a read-out printer responsive to signals generated by the computer to produce a printed record of the signals stored in the computer, whereby activation of the actuating device will cause the computer to start the recorder and audibly present questions seriatum to the patient and cause the light emitting elements to illuminate to display a desired simulated pain or discomfort pattern on the front surface of the model, the answer code signals to the audibly presented questions being stored in the computer together with the respective question code signals and patient identification code signal and thereafter the computer will cause the printer to produce a printed coordinated read-out of the accumulated information.

2. The system as claimed in claim 1 in which said keyboard has mechanical means operable by the patient for giving a YES answer, a NO answer of an I DON'T KNOW answer to each question.

3. The system as claimed in claim 2 in which said mechanical means includes means for indicating to the patient the answer he has given.

4. The system as claimed in claim 3 in which said means for indicating the answer given includes an annunciator light associated with each mechanical means for giving a particular answer.

5. The system as claimed in claim 1 including means for presenting a visual display of each question simultaneously with the audio presentation of each question, said visual display means being connected to and operated by said computer.

6. The system as claimed in claim 1 in which the energy transmitting conduits are electrical wires and the light emitting elements are bulbs.

7. The system as claimed in claim 1 in which the light emitting elements are light emitting diodes and the energy transmitting conduits are fiber-optic bundles.

8. The system as claimed in claim 1 in which at least the patient response device and the human figure model are positioned in a booth, the model being located on a wall of the booth with the front surface outstanding therefrom and the response device located immediately below the model.

9. The system as claimed in claim 1 in which a selected first group of light emitting elements are operable to be illuminated on presentation of a first question and remain illuminated during the patient response followed by illumination of a selected second group of light emitting elements associated on the front surface of the model with the first group to similate a dynamic pain or discomfort pattern.

10. The system as claimed in claim 1 in which the human figure models include a front male figure, a front female figure, a rear figure, a front heat figure and a rear head figure.

11. The system as claimed in claim 1 in which the keyboard comprises a telephone handset, a dial-free overlay member positioned on the dial-face of the telephone, the overlay member having indicia thereon designating particular responses which may be given by the patient to the questions by operating the call control member of a telephone.

12. The system as claimed in claim 11 in which the telephone in a Touch-Tone telephone with buttons on the dial-face thereof and the overlay member has openings corresponding in number and orientation with the buttons to permit the buttons to pass through the overlay member and extend thereabove.

* * * * *

UNITED STATES PATENT AND TRADEMARK OFFICE
CERTIFICATE OF CORRECTION

PATENT NO. : 3,934,226
DATED : January 20, 1976
INVENTOR(S) : STANFORD C. STONE, et al It is certified that error appears in the above-identified patent and that said Letters Patent are hereby corrected as shown below:

Column 2, line 61, change "recroded" to -- recorded --, Column 5, line 51, change "or" to -- of --, Column 6, line 9, change "if" to -- of --, column 6, line 14, omit the period before the question mark, Column 6, line 23, change "beome illuninated" to -- become illuminated --, Column 10, line 14, change "of" to -- or --, and Column 10, line 60, change "in" to -- is --.

Signed and Sealed this

Sixth Day of July 1976

[SEAL]

Attest:

RUTH C. MASON
*Attesting Officer*

C. MARSHALL DANN
*Commissioner of Patents and Trademarks*